United States Patent
Andreiko

(10) Patent No.: US 6,712,607 B2
(45) Date of Patent: *Mar. 30, 2004

(54) ORTHODONTIC BRACKET FOR VISUAL POSITIONING

(75) Inventor: Craig A. Andreiko, Alta Loma, CA (US)

(73) Assignee: Ormco Corporation, Orange, CA (US)

(*) Notice: Subject to any disclaimer, the term of this patent is extended or adjusted under 35 U.S.C. 154(b) by 31 days.

This patent is subject to a terminal disclaimer.

(21) Appl. No.: 10/044,282

(22) Filed: Jan. 11, 2002

(65) Prior Publication Data

US 2002/0058228 A1 May 16, 2002

Related U.S. Application Data

(63) Continuation of application No. 09/422,495, filed on Oct. 21, 1999, now Pat. No. 6,358,044, which is a continuation of application No. 08/933,269, filed on Sep. 18, 1997, now Pat. No. 5,993,206, which is a continuation of application No. 08/641,903, filed on May 2, 1996, now abandoned.

(51) Int. Cl.[7] .............................................. A61C 3/00
(52) U.S. Cl. ............................................................ 433/9
(58) Field of Search ............................ 433/8, 9, 10, 16, 433/17, 24

(56) References Cited

U.S. PATENT DOCUMENTS

| | | |
|---|---|---|
| 3,345,745 A | 10/1967 | Muller |
| 3,936,939 A | 2/1976 | Faunce |
| 4,386,908 A | 6/1983 | Kurz |
| 4,415,330 A * | 11/1983 | Daisley et al. ............... 433/16 |
| D302,588 S | 8/1989 | Jones |
| 5,022,854 A | 6/1991 | Broughton et al. |
| 5,542,844 A | 8/1996 | Perret, Jr. |
| 5,993,205 A | 11/1999 | Heiser et al. |
| 5,993,206 A | 11/1999 | Andreiko |
| 6,358,044 B1 * | 3/2002 | Andreiko ...................... 433/9 |

* cited by examiner

Primary Examiner—Ralph A. Lewis
(74) Attorney, Agent, or Firm—Wood, Herron & Evans, L.L.P.

(57) ABSTRACT

Orthodontic appliances such as orthodontic brackets are provided with bases that are shaped to correspond to the profiles of the specific teeth to which they are to be attached. The shapes of the bases facilitate the visual placement of the appliances on the teeth of patients by visually signaling to the practitioner the positioning of the appliance with the base thereof centered on the facial side of the tooth. This invention further facilitates the positioning of an archwire support of the appliance at a position on a tooth that is offset from the facial axis or from the center of the face of the tooth by manufacture of the appliance with the support offset from the center of the tooth-shaped pad. Preferably, the appliance base is a scaled reduction of the profile of the tooth, viewed from its facial side. The base is preferably scaled differently in the vertical and horizontal directions, with the shape of the base being reduced from that of the tooth profile by a greater amount vertically than horizontally. The tooth-shaped bases further facilitate identification of the specific tooth for which the appliance is intended.

7 Claims, 4 Drawing Sheets

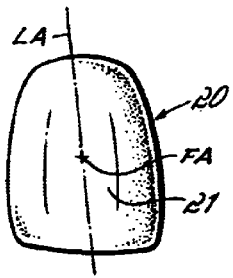
FIG. IA
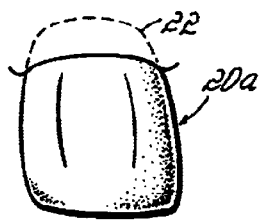
FIG. IB
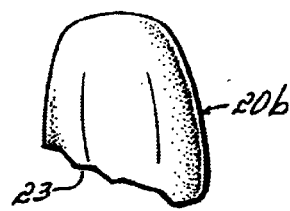
FIG. IC
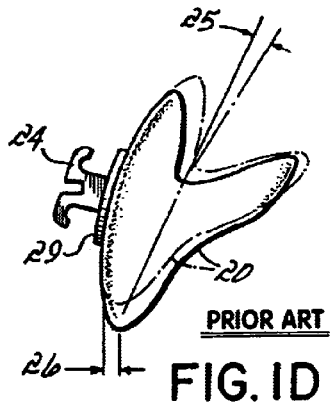
FIG. ID PRIOR ART
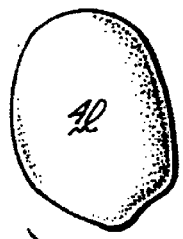
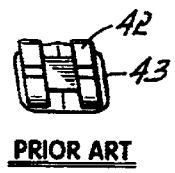 PRIOR ART
FIG. IE
FIG. IF PRIOR ART
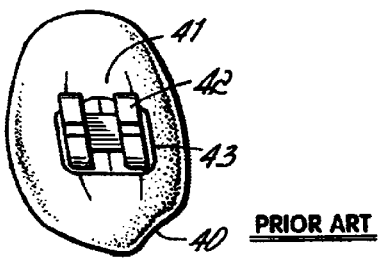
FIG. IG PRIOR ART
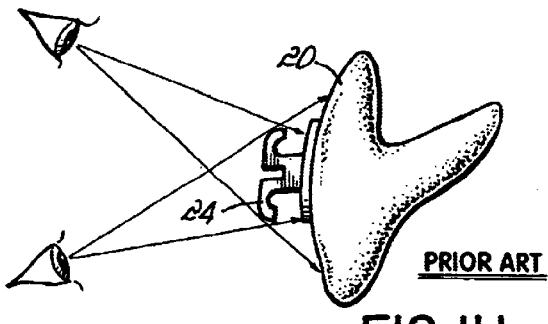
FIG. IH PRIOR ART

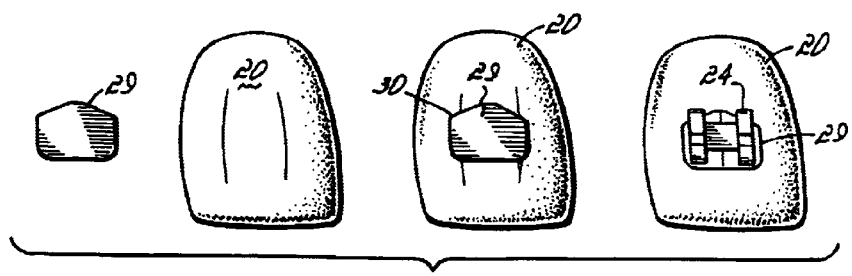
PRIOR ART
FIG. 2
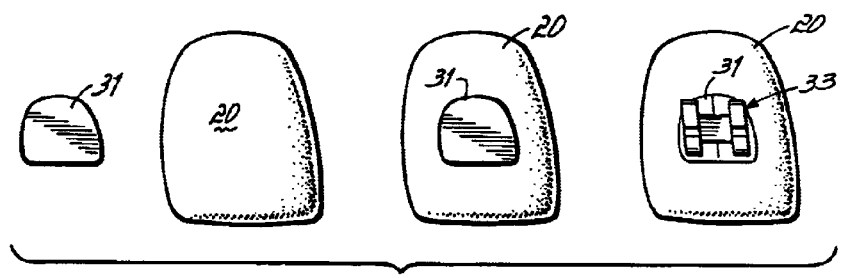
FIG. 3
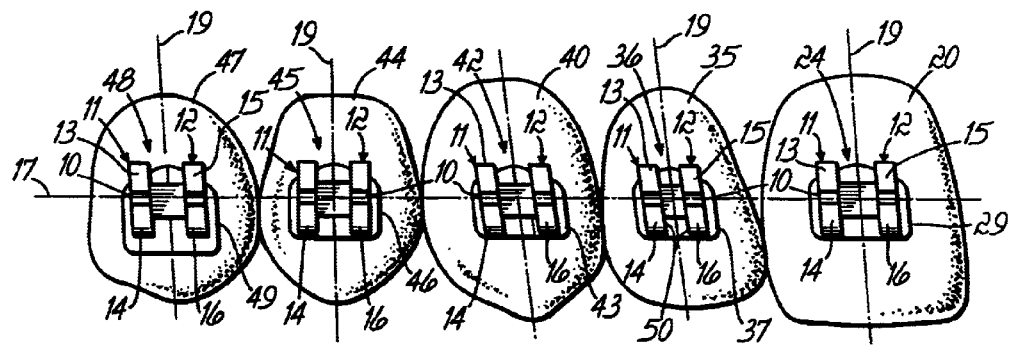
PRIOR ART
FIG. 4A
FIG. 4B

ORTHODONTIC BRACKET FOR VISUAL POSITIONING

This application is a continuation of U.S. patent application Ser. No. 09/422,495, filed Oct. 21, 1999 now U.S. Pat. No. 6,358,044 which is a continuation of U.S. patent application Ser. No. 08/933,269, filed Sep. 18, 1997, now U.S. Pat. No. 5,993,206, which is a continuation application of abandoned U.S. patent application Ser. No. 08/641,903, filed May 2, 1996 abandoned, both entitled "Visual Positioning Orthodontic Appliance and Method", all hereby expressly incorporated by reference herein.

FIELD OF THE INVENTION

This invention relates to the positioning of orthodontic appliances on the teeth of a patient, and more particularly, to the configuration of orthodontic appliances, particularly orthodontic brackets, for the visual positioning thereof on the teeth of patients.

BACKGROUND OF THE INVENTION

When bonding orthodontic appliances, a major tenet to be considered by the orthodontist is the location of the appliance in the mouth of the patient. In the case of bonded orthodontic brackets, this location is the position and orientation of each of the brackets on one of the teeth of the patient.

Most of the preadjusted appliances that are currently employed for maxillary application are designed to be located at the facial axes of the maxillary teeth of the patient. The facial axis, or FA point of a tooth illustrated as Point FA in FIG. 1A, is defined as dead center vertically on the clinical facial surface of a fully erupted crown and at the height of contour mesiodistally of the mid-developmental lobe of the tooth, for example, right maxillary central 20. This definition is based on the criteria that the plane of the archwire will pass through the point FA. Furthermore, appliances should be aligned angularly in the FA plane, which is the plane tangent to surface of the tooth at the FA point, at a line angle represented by line LA in FIG. 1A. This angle LA generally coincides with the line along the height of the contour of the tooth's mid-developmental lobe 21. So angularly aligned, the appliance will better deliver the appropriate final angular position or tip of the tooth. These criteria are referred to as the concept of morphological centering and angular alignment. This concept is quite often implemented visually by the orthodontist or other clinician who places the appliance on the tooth by making a visual determination of the location of the point FA and the orientation of the line LA. The visual implementation of this concept can be rendered difficult for the orthodontist by varying degrees of eruption that leaves an unerupted portion 22 of a tooth 20a, as illustrated in FIG. 1B, by virtue of chipped or worn incisal tooth edges 23 of a tooth 20b, as illustrated in FIG. 1C, or by virtue of the existence of other aberrations of the typical tooth profile. Teeth for mandibular application are also often visually placed in accordance with mandibular placement criteria.

While the concept of morphological centering and angular alignment is familiar to orthodontists, the clinical difficulty of achieving its placement goals is well known. Several approaches have been developed to alleviate this problem but all have drawbacks. The most common approach has been to use measuring instruments to position the appliances at fixed vertical heights. These heights typically represent something akin to the average distance from the incisal edge of a tooth to the FA point of the tooth, and are usually expressed in millimeters. The awkwardness of this approach is that teeth come in various sizes, which precludes placement of the appliance at the proportional center of the tooth in all but the truly average patient. Additionally, due to the highly probably presence of a malocclusion and to the lack of access because of the tooth's position in the mouth (e.g. as with posterior segments or crowding) there is often insufficient space to use these instruments effectively.

When the appliances are not placed at the design location, adverse effects occur with respect to the final positioning of the teeth. First, if the appliance such as an upper right central bracket 24 is placed incorrectly in the vertical plane, the faciolingual inclination of the tooth is effected, producing an inclination error 25 as illustrated in FIG. 1D. Secondly, at the same time, the apparent thickness of the appliance is effected, resulting in a labial-lingual offset error 26 from the desired placement of a tooth on the dental arch.

Another approach to this problem is that known as "indirect bonding." This approach involves positioning of the appliances on a model or cast of the patient and then using a transfer mechanism or tray to transfer the positioned appliances to corresponding positions on the teeth of the patient. The indirect bonding approach has its detracting features. For instance, often the tray does not seat fully, causing simultaneous incorrect placement of a multitude of individual appliances. Other problems include appliance adhesive failure and excessive "flash." Further, brackets are typically, although not always, placed by eye on the model, which offers little improvement over direct placement on most patients. These difficulties have been sufficient to severely limit the use of the indirect bonding technique.

An understanding of why the centering and aligning of appliances has been so clinically troublesome can be obtained by examining the morphology of the appliances and the dentition. Teeth, as most anatomical entities, have a generally flowing shape which does not lend itself to description or visualization using geometric determinants, as can be seen from the profile of a typical upper right cuspid 40 in FIG. 1E. Appliances such as brackets and their bonding pads, on the other hand, are typically generated from orthogonal geometric designs that lend themselves to ease of appliance manufacture, as can be seen from a typical upper right cuspid bracket 42. Further complicating this situation with respect to vertical placement is the varying torque or inclination angle of the archwire slot relative to the base of the appliance. This occurs whether an angle of a slot is cut in a bracket support, i.e. "torque in the face", or an angle is formed in the mounting surface of a bracket, e.g., "torque in the base". Because of this angle, the true plane of the archwire, which should intersect the FA point, is difficult for the orthodontist to visualize. Thus, positioning of the appliance, such as with the illustrated high torque upper right central bracket 24a, using either the bracket body or the facial view of the slot, will yield the positioning of the bracket on a tooth, such as tooth 20, with the archwire plane AWP intersecting the tooth 20 at a point displaced from the point FA, by an amount 28, as illustrated in FIG. 1F. Such a view afforded the clinician when placing the appliances often incorrectly influences the positioning. For the clinician to attempt to minimize this problem by viewing directly into the slot of the appliance during placement is at least awkward and not always possible clinically.

Additionally, when placing the appliance mesiodistally, the geometric appearance of the bracket and bonding pad can also be misleading, as seen when the rhomboid geometry of some individual appliances is compared to the dental anatomy. For example, FIG. 1G illustrates the difference between the shapes of orthogonal upper right cuspid bracket 42 and the anatomical shape of the upper right cuspid 40 with the bracket 42 correctly placed on mid-developmental lobe 41 that is not coincident with the mesiodistal center of the tooth. Further, when a clinician uses the bracket body portion of an appliance as the primary landmark, parallax is also a complicating circumstance that gives the clinician an incorrect apparent view of appliance position, as illustrated in FIG. 1H.

Notwithstanding the problems and disadvantages stated above, the concept of visual positioning of orthodontic appliances on the teeth of patients remains a technique that clinicians must use. Therefore, there remains a need for a solution to the problems of the prior art and for greater accuracy and reliability in visual appliance positioning.

SUMMARY OF THE INVENTION

A primary objective of the present invention is to alleviate the deficiencies of the prior art appliances that render inefficient and imprecise the visual positioning of orthodontic appliances on the teeth of patients. It is a particular objective of the present invention to provide an orthodontic appliance that provides a visual signal to the clinician that enhances the ability and the likelihood of achieving precise and accurate placement of the appliance on the teeth of a patient.

In accordance with the principles of the present invention, the orthodontic appliance, and particularly the portion thereof that lies against the tooth of a patient, is contoured in a way that corresponds to the profile of the tooth on which the appliance is to be positioned, so as to provide a signal that guides the clinician in the easy and precise positioning of the appliance on the tooth. It is a particular objective of the present invention to provide orthodontic appliances with tooth mounting surface thereon that are shaped to provide to the clinician who is placing the appliance on the tooth of a patient a placement signal that will facilitate the centering of the appliance on the tooth of the patient and will override erroneous signals that are caused by irregularities in the actual profile or shape of the patient's teeth.

In accordance with the preferred embodiment of the invention, orthodontic appliances such as orthodontic brackets are provided with bases of pads that have shapes related to the frontal anatomies of the specific respective teeth to which the appliance is to be attached. The archwire support portion of the appliance is, in one embodiment, fixed relative to the pad so that the plane of the archwire passes through the FA point of the tooth when the pad is properly positioned on the tooth. In alternative embodiments, the wire support portion of the bracket is fixed to the pad, extending rigidly from the pad, so that the archwire plane intersects the tooth at a position other than through the FA point that meets some intended placement criteria offset from the FA point.

In one preferred embodiment of the invention, the archwire support portion of a bracket is fixed to a pad so that the pad can be positioned upon the mesiodistal center of the tooth by a visual centering of the tooth in a facial view with the bracket at the height of the contour of the mid-developmental lobe. Such support portions are fixed to the pad, either by being formed separate from the pad and being attached to the pad by welding, fusing or other bonding technique or by being formed integral with the pad in a molding, forging, casting, machining or other such manufacturing operation. The brackets being so formed, the support portion extends rigidly from the pad and is located on the opposite side of the pad from the mounting surface at which the pad is to be attached to a tooth. The position of the archwire support on the pad may be defined in relation to a point on the mounting surface, thereby making it possible to locate the support by properly positioning the pad on a tooth.

In accordance with the principles of the present invention, the bases or mounting pads of the appliances are shaped to conform to the outlines or profiles of the teeth to which the bases are to attach. The profiles are preferably the silhouettes of the specific teeth when viewed from the facial side of the tooth in a lingual direction in the archwire plane. The sizes of the pads, so shaped, are preferably geometrically reduced or scaled down from the sizes of the profiles of specific teeth. The profile shapes are preferably statistically average shapes for each tooth type among the members of a population segment. The appliances having bases so shaped send to the clinician, who is mounting the appliances on the teeth of a patient, a strong visual signal, which, when received by the eye of the clinician, guides the clinician in the placement of the appliances at the visual centers of the teeth. With the bases or pads to be so located, the archwire support portions of the appliances can be either centered on the bases or offset from the centers of the bases so that they assume their intended positions on the teeth.

With the preferred embodiment of the invention, the shapes of the pads or bases of the appliances are determined by producing an outline or profile of the tooth as would be seen by the installing clinician from the facial side of the teeth. This outline is then scaled downward in size to a size that is appropriate for the appliance base or pad. The size reduction of the shapes from that of the tooth outline to that of the finished appliance base or pad may be carried out according to a scale that differs in the horizontal and vertical directions. For example, a bracket pad may be scaled in the horizontal direction to 50% of the horizontal dimension of the tooth while being scaled in the vertical direction to 25% of the dimension of the tooth.

The appliances of the present invention and the methods of making and placing such appliances provide the advantages of more efficient and precise visual placement of the appliances on the teeth. In addition, such appliances and methods provide for a reduction in bracket adhesive failure, since the shaped pads may easily have at least a twenty percent increase in bonding area, and in some cases, much more. This increase may be provided without noticeable deterioration in esthetics by carefully enlarging the pad only in areas where the increase would be unnoticed when a ligature and archwire are present. This is accomplished while still maintaining the anatomical placement registration.

In addition, the difficulty of excess adhesive cleanup is reduced because the pads have no sharp corners, so that cleanup can be achieved with fewer discreet moves than with an orthogonal pad. Additionally, the tie wings of the brackets can be more easily made so as not to extend beyond the pad and therefore be less likely to snag on the cleanup instrument and thereby dislodge or alter the position of the appliance. Also, the likelihood of appliance drift prior to adhesive polymerization is further reduced because the ratio of the area of the pad to the mass of the assembly is greater in relation to that of the standard orthogonal pad, thereby lessening the propensity for the appliance to move due to gravity before the adhesive polymerizes.

A further advantage of the tooth-shaped pad is that the pad itself serves as a bracket identifier that is different for each tooth type and also for each quadrant, because the tooth-shaped pads carry tooth specific anatomic information that visually describes which tooth the appliance is designed for, simplifying identification of the particular appliance.

Patient hygiene and iatrogenic decalcification are improved with the tooth-shaped pads because the bracket tie wings need not exceed the perimeter of the pads, and therefore the patient is able to access this area with a toothbrush to minimize the decalcification commonly seen at the gingival edge of the pad. Additionally, the pads may be designed to cover the gingival areas where decalcification is common.

The quality of pad fit with respect to tooth curvatures is further increased with the pads shaped according to the present invention, because, while the pad of a standardized bracket is unlikely to fit any tooth perfectly, the tooth-shaped pads have less in the way of corners than do orthogonal pads, so teetering across the diagonal corners of the orthogonal pads is lessened.

The present invention is particularly advantageous in the application of appliances to the maxillary teeth, although certain features of the invention provide advantages in the application of appliances to mandibular teeth.

These and other objectives and advantages of the present invention will be more readily apparent from the following detailed description of the drawings of the preferred embodiment of the invention, in which:

BRIEF DESCRIPTION OF THE DRAWINGS

FIGS. 1A through 1H are a series of diagrams illustrating problems in the visual placement of orthodontic appliances on teeth with appliances of the prior art.

FIG. 2 is a series of diagrams illustrating the prior art placement of a conventional appliance on a tooth.

FIG. 3 is a series of diagrams illustrating the placement on a tooth of an appliance embodying principles of the present invention.

FIG. 4A is a facial diagram illustrating the prior ad placement of a set of conventional brackets on right maxillary teeth, while FIG. 4B is a similar diagram illustrating the placement on right maxillary teeth of tooth-shaped brackets according to principles of the present invention.

DETAILED DESCRIPTION OF THE DRAWINGS

Figure 5A:
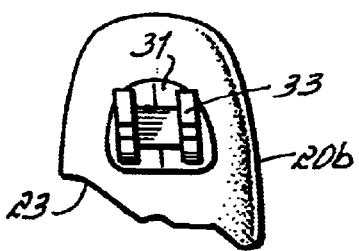
FIGS. 5A–5B and FIGS. 5C–5D are facial diagrams comparing the placement of the appliances of FIG. 3 and FIG. 2, respectively, in situations where the outline of the tooth on which it is placed is unclear.
Figure 5B:
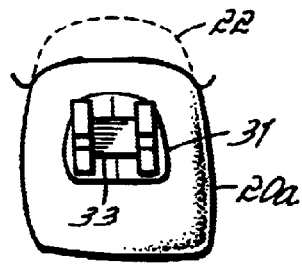
Figure 5C:
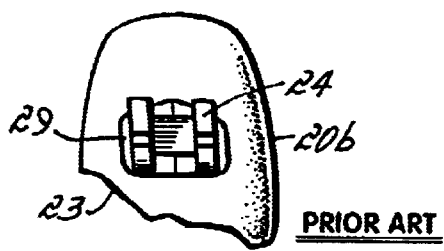
Figure 5D:
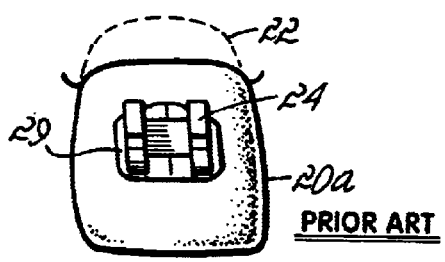

The present invention recognizes that many errors occurring in the orthodontic positioning of appliances on teeth are caused by erroneous visual signals that result from a lack of similarity between different shapes. With the present invention, the appliance is rendered easy to position by providing the bonding pad to which the appliance is precisely fixed with a shape related to the outline of the tooth to which it is to attach. With the present invention, the bracket is located with sufficient precision on the pad, which results in variations in placement being lessened by the more dominant visual signal sent to the clinician due to the congruity of the pad and the dental anatomy. With the preferred embodiment of the invention, brackets are provided with pads that, for each tooth type, are shaped to conform to the dental anatomical outlines of the specific tooth of the type to which the bracket is to attach, with geometric reductions then performed on the pad shapes for each tooth type to create reduced size shapes that send more "signal" to the eye of the clinician.

FIG. 2 illustrates the outline of a pad 29 of a conventional maxillary right central bracket, the outline of the maxillary right central tooth 20, the pad outline 29 properly positioned on the tooth 20, and the assembled conventional bracket 24 with its pad 29 positioned on the tooth 20. The pad 29 of the bracket 24 has a standard orthogonal shape. As can be seen from FIG. 2, when centered on the tooth 20, the upper left corner 30 of the pad 29 is the closest to the perimeter of the profile of the tooth 20, making the pad 29 and bracket 24 appear to be off center to the left. Such a visual signal has a tendency of causing the clinician to place the bracket 24 on the tooth slightly to the clinician's right of its proper position.

Referring to FIG. 3 is illustrated the outline of a pad 31 of a maxillary right central appliance according to principles of the present invention. The pad 31 has the same general peripheral shape as the outline of the maxillary right central tooth 20. When the pad 31 is properly centered on the tooth 20, the outline of the pad 31 is proportionately spaced from the outline of the profile of the tooth 20 and appears visually centered on the tooth 20. Thus, a maxillary right central bracket 33 that is similar to the standard bracket 24 but has the tooth-shaped pad 31 has the visual appearance of being centered on the tooth 20. Such a tooth-shaped pad 31 gives a visual signal to the clinician who is placing the bracket 33 on the tooth 20 that the bracket 33 is properly centered on the tooth 20. With the pad 31 of the bracket 33 so shaped to conform to the outline of a maxillary right central 20, the practitioner receives this visual signal that causes the pad 31 to appear to "snap" into place visually, whereas no such visual signal is produced by the orthogonal design of the pad 29. Preferably, the pad 31 is shaped to conform to the profile or outline of a statistically average maxillary right central of a population segment that is representative of the patient being treated with the appliance 33.

The pads of brackets of the present invention are preferably each designed for the different specific teeth of a patient. For each of the specific teeth of a patient (for example, for the maxillary right central 20, lateral 35, cuspid 40, first bicuspid 44 and second bicuspid 47), standard orthogonal brackets 24, 36, 42, 45 and 48 differ usually primarily in that the sides of their respective pads 29, 37, 43, 46 and 49 are parallel to the wings 50 of the brackets and correspond to the tip of the axis 19 of the respective tooth, as illustrated in FIG. 4A. Such a bracket configuration is described in U.S. Pat. No. 4,415,330 of Daisley et al., hereby expressly incorporated by reference herein. The brackets 24, 36, 42, 45 and 48 of FIG. 4 and of the Daisley et al. patent each have distal and mesial tie wings 11 and 12, respectively. The distal tie wings 11 are fixed to the respective bracket base pads 29, 37, 43, 46 and 49 and each includes a gingival tip 13 and an occlusal tip 14. The mesial tie wings 12 are also fixed to the respective base pads and each includes a gingival tip 15 and an occlusal tip 16. The respective gingival and occlusal tips define between them an archwire slot 10. The distal and mesial tie wings 11 and 12 have parallel distal and mesial sides. The archwire slot 10 provides a reference line 17 in the archwire plane AWP for orientation parallel to the occlusal plane of a patient. The sides of the tie wings 11 and 12 are inclined at an oblique angle to the reference line 17, so that the tie wings 11 and 12 can be generally vertically disposed parallel to the tooth long axis 19 and still be inclined at an oblique angle to the reference line 17. The gingival tips 13 and 15 and the occlusal tips 14 and 16 of respective tie wings 11 and 12 have top and bottom surfaces that are substantially equidistant from, and in mutual alignment parallel to, the reference line 17. The tie wings 11 and 12 together form a rhomboidal configuration and the axis of the archwire slot bisects the tie wings 11 and 12 50 that the gingival tips 13 and 15 and the occlusal tips 14 and 16 are of equal size.

With the appliances of the present invention, brackets 33, and 51–54 are provided with pads 31, and 55–58 that are shaped to conform respectively to the outlines of the profiles of average teeth, 20, 35, 40, 44 and 47, as illustrated in FIG. 4B. Such pads, shaped so as to conform to the outlines of these teeth, are similarly illustrated. Such shapes additionally identify the brackets 33, 51–54 as being intended for the specific respective teeth 20, 35, 40, 44 and 47. These tooth-shaped pads are illustrated in FIG. 46 in combination with the bracket archwire supports of the Daisley et al. patent described above.

Figure 6A:
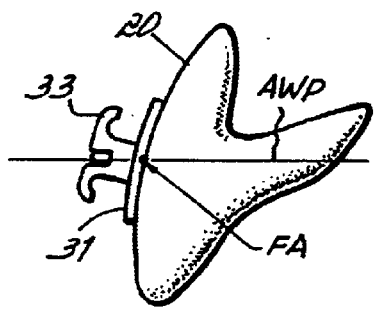
FIGS. 6A and 6B are mesial diagrams illustrating effective placement of the appliance of FIG. 3 for both standard and high torque prescriptions.
Figure 7:
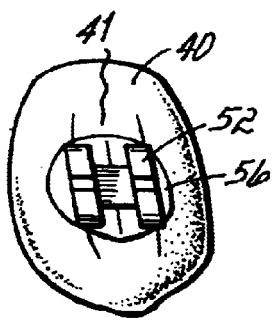
FIG. 7 is a facial diagram illustrating how off center placement of a bracket support can be achieved with the present invention.

With the tooth-shaped pads 31 and 55–58, calculated and precise location of the support portion of the brackets 33 and 51–55 upon the pads assures that the archwire plane AWP passes through the anatomical center of the pad irrespective of the particular appliance prescription chosen by the clinician. For example, as illustrated in FIGS. 6A and 66 respectively, for a bracket 33 having a standard prescription and for a bracket 33a having a high torque prescription, the true archwire plane AWP will tend to pass through the FA point with visual placement of the bracket 33 or 33a on the tooth 20. In addition, as illustrated in FIG. 7, when brackets having tooth-shaped pads are employed on teeth having a mid-developmental lobe 41 that is not in the middle of the facial view of the tooth, such as for the illustrated maxillary cuspid 40, the bracket 52 can accommodate the off-center lobe 41 by an adjusted placement of the bracket 52 on the pad 56, so that when the pad 56 is placed on the facial center of the tooth 40, the bracket will be mesiodistally displaced an appropriate amount. Compared with the bracket 42 having the standard orthogonal bracket pad 43 (FIG. 4A), the visual placement of the bracket 52 places the bracket 52 at the height of contour of the mid-developmental lobe 41 of the tooth 40, while the pad 56 will be placed by the clinician at the center in the facial view of the tooth 40.

Figure 8:
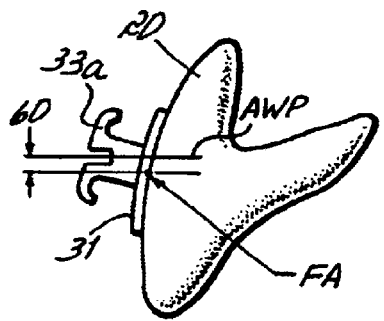
FIG. 8 is a mesial diagram illustrating an appliance positioned with a vertically offset archwire plane in accordance with an embodiment of the present invention.

Also, the tooth-shaped bracket, such as the bracket 33a, can easily be designed so as to offset the archwire plane AWP vertically from the classic FA point on the tooth, for example, tooth 20, by a predetermined amount where the appliance is intended for such placement, as illustrated in FIG. 8. Such an offset position is likely to be accepted as a preferred modification to classic placement as the clinical bracket positioning art matures and more clinical evidence with respect to ideal placement is obtained. Such a bracket 33a is fixed so its support is at a vertical offset position on pad 31, which is still centered on the tooth 20 by visual placement, to give placement of archwire plane AWP by a predetermined distance 60 that is above or below FA point if desired.

The preferred method of the invention for determining the shapes of the bases of the appliances described above includes first producing outlines or profiles of each of the teeth of a patient, or of the teeth of a class of patients using statistical tooth shape data so that a standard outline for each tooth type, i.e., cuspid, central, etc., is produced. Preferably, each standard outline corresponds to a statistically average shape for all patients or statistical group of patients. From such outlines, a scaled down representation of each tooth shape is generated by reducing the tooth profiles in size to the desired sizes of the appliance bases. The size reduction may be uniform in all directions, but, preferably, different scales are used for different coordinates, such as by employing different vertical and horizontal dimension reductions. Most preferred is the use of a greater reduction of the vertical dimensions than of the horizontal dimensions, for example, by making the pads to a size of from 20 to 40% of the corresponding vertical dimensions of the tooth shape outlines and to from 40 to 60% of the corresponding horizontal dimensions of the tooth shape outlines.

Figure 9:
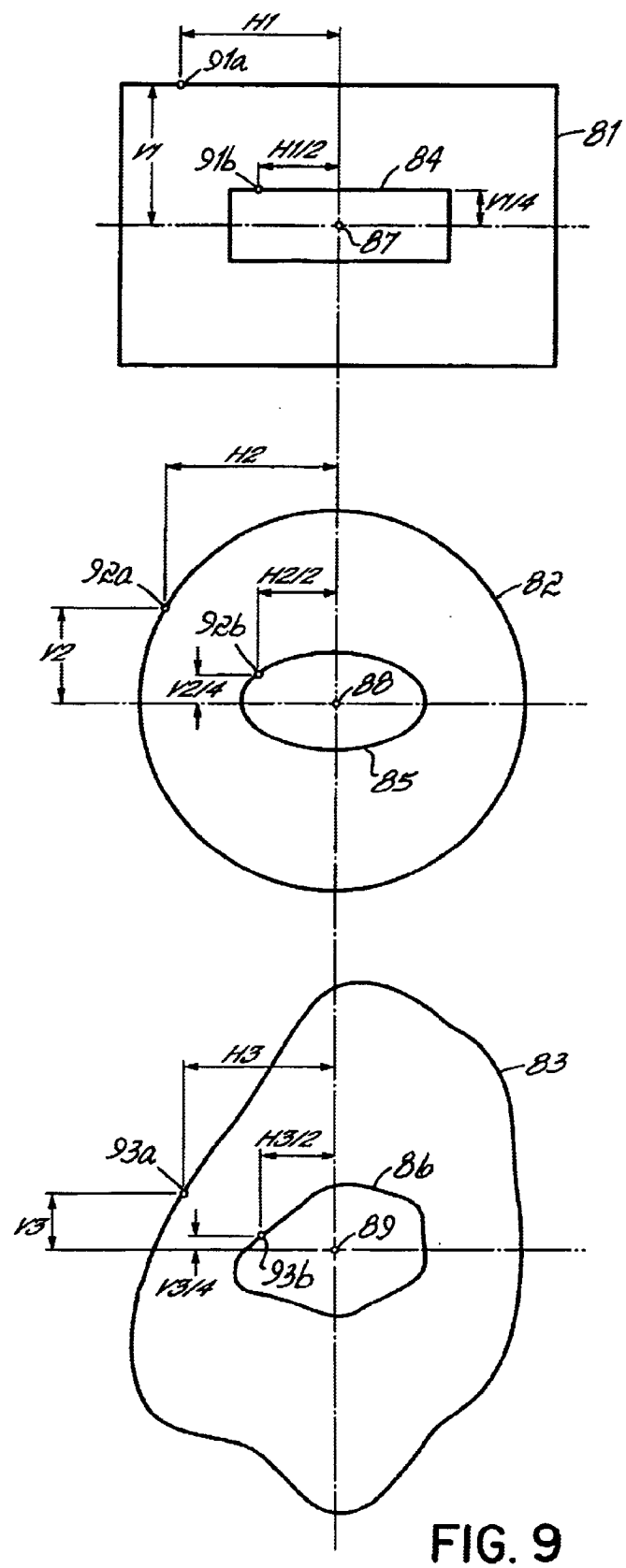
FIG. 9 is a series of diagrams illustrating one preferred manner of proportionally scaling the shape of the tooth profile to arrive at tooth-shaped brackets of the preferred embodiment of the present invention.

In FIG. 9 are illustrated a scaling of the outlines of a representative square profile 81, a circular profile 82 and an arbitrary shape 83 that can be regarded, for illustration purposes, as representative of the shape of a tooth. In each of the profiles 81–83 is respectively illustrated a correspondingly shaped form 84–86 which may be considered representative of the shape of an orthodontic appliance base or pad. The preferred method of proportionate size reduction used in each illustrated case scales the profiles by different amounts vertically and horizontally. The reduction illustrated uses a 25% scale factor in the vertical direction and a 50% scale factor in the horizontal direction. The centers of the profiles of each of the original shapes 81–83 are indicated at 87–89, respectively, on which the shapes of the pads 84–86 are respectively centered. Corresponding points on the corresponding shapes of the tooth outline and the pad outline, for example, points 91a and 91b, points 92a and 92b and points 93a and 93b, are respectively moved in the scaling step, vertically to one fourth of the original vertical distances $V_1$, $V_2$, $V_3$ from the horizontal centerlines, and horizontally one half of the horizontal distances $H_1, H_2, H_3$ from the vertical centerlines.

The appliances for which the present invention is most useful are the maxillary incisors, cuspids and bicuspids, on which the appliances are most often and most easily positioned visually.

Accordingly, those skilled in the art will appreciate that the application of the present invention herein are varied, that the invention is described in preferred embodiments, and that additions and modifications can be made without departing from the principles of the invention. Therefore, the following is claimed:

What is claimed is:

1. An orthodontic bracket configured for placing on a tooth that is a unique one of the teeth of any of a plurality of patients, an orthodontic appliance comprising:
   a bonding base adapted to be secured with adhesive to the facial side of said tooth of a patient;
   an archwire support extending rigidly from the base and having an archwire slot so positioned and oriented therein as to move said tooth to a predetermined treatment position and orientation when the base is centered on the facial side of said tooth;
   the base having a perimeter that is visually perceivable when placed against the facial side of the toot and has a shape that is a scaled reduction of the characteristic outline of said unique one of the teeth when viewed from the facial side of said tooth, whereby the base is centered and aligned on the facial side of said tooth when the perimeter of the base is congruent with the outline of the toot;

the archwire support including a distal tie wing and a mesial tie wing, the tie wings being each fixed to said base and each including a gingival tip and an occlusal tip, the tips defining between tern an archwire slot, each of the tie wings having parallel distal and mesial sides, the archwire slot providing a reference line, the sides of the tie wings being inclined at an oblique angle to the reference line;

whereby the archwire slot is orientated parallel to the occlusal plane of a patient and the tie wings are inclined at an oblique angle to the reference line and generally vertically disposed parallel to the tooth long axis when the base is placed on the facial side of said tooth and the position and orientation of the bracket is visually adjusted on said toot so that the perimeter of the base is congruent with the outline of said tooth; and the gingival tips and occiusal tips of the tie wings having respectively top and bottom surfaces which are in mutual alignment parallel to the reference line and substantially equidistant therefrom; and the tie wings together forming a rhomboidal configuration and the axis of the archwire slot bisecting the tie wings so that the gingival tips and the occiusal tips are of equal size.

2. The bracket of claim 1 wherein:

the perimeter of the base of the bracket is a scaled reduction that is a replication, proportionately reduced in size of a standard profile that is uniquely characteristic of the typical shape of the unique one of the teeth a different specific one of the different teeth of a representative plurality of human patients.

3. The bracket of claim 2 wherein:

the perimeter is a scaled reduction that is a replication, proportionately reduced in size by one scale vertically and by another scale horizontally, of said standard profile.

4. The bracket of claim 3 wherein:

the perimeter of the base is a replication of the shape of said standard profile, proportionately reduced in size vertically and horizontally, with the reduction vertically being greater than the reduction horizontally.

5. The bracket of claim 4 wherein:

the perimeter of the base is a replication of the shape of said standard profile, proportionately reduced in size to between 20% and 40% of the vertical dimensions of the profile and to between 40% and 60% of the horizontal dimensions of said standard profile.

6. The bracket of claim 5 wherein:

the perimeter of the base is a replication of the shape of said standard profile, proportionately reduced in size to approximately 25% of the vertical dimensions of the profile and to approximately 50% of the horizontal dimensions of said standard profile.

7. The bracket of claim 1 wherein:

the perimeter of the base of the bracket corresponds to the anatomically average shape of the unique one of the teeth teeth of the representative plurality of human patients.

* * * * *

UNITED STATES PATENT AND TRADEMARK OFFICE
CERTIFICATE OF CORRECTION

PATENT NO.     : 6,712,607 B2
DATED          : March 30, 2004
INVENTOR(S)    : Craig A. Andreiko It is certified that error appears in the above-identified patent and that said Letters Patent is hereby corrected as shown below:

Column 5,
Line 39, reads "illustrating the prior ad placement of a set" and should read
-- illustrati ng the prior art placement of a set --.

Figure 6B:
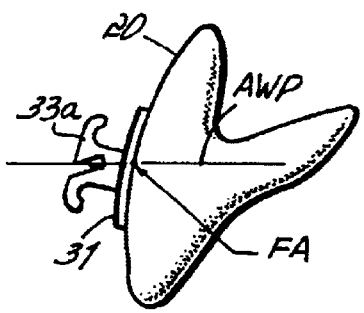

Column 7,
Line 17, reads "the tie wings 11 and 12 50 that the" and should read -- t he tie wings 11 and 12 so that the --.
Line 28, reads "illustrated in FIG. 46 in" and should read -- illustra ted in FIG. 4B in --.
Line 36, reads "illustrated in FIGS. 6A and 66" and should read -- i llustrated in FIGS. 6A and 6B --.

Column 8,
Line 45, reads "the application of the present invention herein are varied, that the" and should read -- t he applications of the present invention herein are varied, that the --.
Line 66, reads "facial side of the toot and" and should read -- facial side of the tooth and --.

Signed and Sealed this

Twenty-eighth Day of December, 2004

JON W. DUDAS
*Director of the United States Patent and Trademark Office*

UNITED STATES PATENT AND TRADEMARK OFFICE
CERTIFICATE OF CORRECTION

PATENT NO.    : 6,712,607 B2
DATED         : March 30, 2004
INVENTOR(S)   : Craig A. Andreiko It is certified that error appears in the above-identified patent and that said Letters Patent is hereby corrected as shown below:

Column 5,
Line 39, reads "illustrating the prior ad placement of a set" and should read
-- illustrati ng the prior art placement of a set --.

Column 7,
Line 17, reads "the tie wings 11 and 12 50 that the" and should read -- t he tie wings 11 and 12 so that the --.
Line 28, reads "illustrated in FIG. 46 in" and should read -- illustra ted in FIG. 4B in --.
Line 36, reads "illustrated in FIGS. 6A and 66" and should read -- i llustrated in FIGS. 6A and 6B --.

Column 8,
Line 45, reads "the application of the present invention herein are varied, that the" and should read -- t he applications of the present invention herein are varied, that the --.
Line 66, reads "facial side of the toot and" and should read -- facial side of the tooth and --.

Column 9,
Line 5, reads "with the outline of the toot;" and should read -- with the outline of the tooth; --.
Line 9, reads "defining between tern an archwire slot," and should read -- defining between them an archwire slot --.
Line 20, reads "on said toot so that the" and should read -- on said tooth so that the --.
Line 22, reads "the gingival tips and occiusal tips of the" and should read -- the gingival tips and occlucal tips of the --.
Line 28, reads "the gingival tips and the occiusal tips are" and should read -- the gingival tips and the occlusal tips are --

Column 10,
Line 1, reads "profile that in uniquely characteristic of the typical shape of the unique one of the teeth a different specific one of the different teeth of a representative plurality of human patients." and should read -- profile that is uniquely characteristic of the typical shape of the unique one of the teeth, a different specific one of the different teeth of a representative plurality of human patients. --.

UNITED STATES PATENT AND TRADEMARK OFFICE
CERTIFICATE OF CORRECTION

PATENT NO. : 6,712,607 B2  Page 2 of 2
DATED : March 30, 2004
INVENTOR(S) : Craig A. Andreiko It is certified that error appears in the above-identified patent and that said Letters Patent is hereby corrected as shown below:

Column 10 (cont'd),
Line 29, reads "shape of the unique one of the teeth teeth of the" and should read
-- shape of the unique one of the teeth of the --.

This certificate supersedes Certificate of Correction issued December 28, 2004.

Signed and Sealed this

Third Day of May, 2005

JON W. DUDAS
*Director of the United States Patent and Trademark Office*